United States Patent [19]
Martin et al.

[11] Patent Number: 5,571,643
[45] Date of Patent: Nov. 5, 1996

[54] SPECTROPHOTOMETRIC QUANTITATION OF IMAGES IN X-RAY FILM AND ELECTROPHORESIS GEL BANDS

[76] Inventors: Mark T. Martin, 9 Prairie Rose La., Gaithersburg, Md. 20878; Rosa I. Sanchez, 2711 Green Hollow Dr., Iselin, N.J. 08830

[21] Appl. No.: 279,192

[22] Filed: Jul. 22, 1994

[51] Int. Cl.$^6$ ............................... G01N 21/77; G01J 3/42
[52] U.S. Cl. ............................... 430/30; 430/347; 436/2; 436/8; 436/80; 436/171; 436/175; 356/326; 356/319; 356/432; 356/443
[58] Field of Search ............................... 430/30, 347; 436/2, 436/8, 80, 171, 175; 356/326, 319, 432, 443

[56] References Cited

U.S. PATENT DOCUMENTS

| | | | |
|---|---|---|---|
| 3,843,325 | 10/1974 | Schmitt et al. | 436/80 |
| 4,876,068 | 10/1989 | Castaneda | 422/58 |
| 4,920,057 | 4/1990 | Castaneda | 436/77 |

OTHER PUBLICATIONS

D. H. O. John & G. T. J. Field, *A Textbook of Photographic Chemistry*, Chapman & Hall Ltd., London, 6–7, (1963).
Holmquist, B., *Methods Enzymol*, 158, 6–14, (1988).
Molecular Dynamics brochures on densitometry instrumentation.
Pharmacia LKB Biotechnology brochure on the ImageMaster™ Electrophoresis Evaluation System.

*Primary Examiner*—Mark F. Huff
*Attorney, Agent, or Firm*—John W. Ryan; Patrick J. Igoe

[57] ABSTRACT

Images comprised of silver such as X-rays and electrophoresis gel bands, wherein the size and darkness of the image provides useful information, are quantitated utilizing a spectrophotometer to quantify the silver which comprises the image. An image is isolated from X-ray film or an electrophoresis gel followed by removal therefrom of any silver which is present. The removed silver is complexed to cause an optical change. A spectrophotomer is then used to measure the absorbance and the absorbance measurement is compared with a calibrated reference standard.

22 Claims, 5 Drawing Sheets

SPECTROPHOTOMETRIC QUANTITATION OF IMAGES IN X-RAY FILM AND ELECTROPHORESIS GEL BANDS

BACKGROUND OF THE INVENTION

The present invention relates generally to the field of reading X-rays, electrophoresis gel bands, and the like wherein the size and darkness of an image provides useful information. More specifically the invention has to do with a method of quantitating images in X-ray film and electrophoresis gel bands utilizing a spectrophotometer to quantify the silver which comprises the image. Presently the conventional method of quantitating such images is by densitometry, a method which can be prohibitively expensive and impractical.

Often in various professions, such as biochemistry, molecular biology, cell biology, dentistry and medicine, X-ray films are developed in which images represent a chemical or tissue. The darkness of the image is proportional to the amount of material present. It is frequently desirable to quantitate the material by judging the darkness or size of the image. Until now, the main way for quantitating images on X-ray film is to use an instrument called a densitometer.

A densitometer can quantitate optical densities, such as those of bands or spots on gels, membranes and autoradiograms. Densitometry can be used in order to create digital records of these samples. Densitometers work by comparing the intensity of light transmitted through a sample with the intensity of light incident on the sample. Thus, densitometers are instruments that are specially designed and manufactured for image quantitation.

For example, the ImageMaster™ Electrophoresis Evaluation System, manufactured by Pharmacia LKB Biotechnology, is available for protein quantification and analysis, and compared to other densitometry instrumentation, purports to be faster and better equipped to scan more types of images. The ImageMaster™ System DTS, has various uses, for instance, scanning wet or dry gels, autoradiographs, blots, photographs, slides, 96-well microtiter plates and Petri dishes. The system comprises a high resolution, white light, transmittance/reflectance desk top scanner (DTS) and computer software. However, the sole use of the spectrophotometer in the present invention eliminates the need for all of these expensive components.

Moreover, the use of a densitometer has two disadvantages when compared with the present invention. The first disadvantage is the cost and specialized use of the densitometer. It is only used for quantitating images, which makes it prohibitively expensive for the occasional user or for laboratories lacking money to buy instruments. The second disadvantage is that a densitometer may be designed only to accept certain sizes and shapes of X-ray film. Until now, no simple inexpensive physical or chemical method existed for quantitating images on X-ray film. The present invention was developed in order to circumvent these problems.

The present invention addresses the problems in the prior art by utilizing a spectrophotometer, an instrument readily available in research and clinical laboratories. The basis for the use of this instrument is the finding that silver, isolated from various sources of images, when bound with a complexing agent, will produce a color change that can be read with the spectrophotometer. The complexing agent, specifically, diphenylthiocarbazone (dithizone) has been known in the art to change colors when complexing with various metals especially in the context of the elimination of adventitious metals. Holmquist, B. (1988) Methods Enzymol. 158, 6–14. However, in the present invention, we have discovered that the complex formed between silver and the dithizone complexing agent has high affinity and a different color than free dithizone thus, making the extent of the color change linearly proportional to the amount of silver added to the dithizone solution. Therefore, upon comparison of the amount of silver in the silver containing image with the amount of silver in a reference spot or a standard curve, the amount of material is readily quantifiable.

Because silver compounds comprise photographic images, one application of this invention is for use in quantitating X-ray film images that represent a given material. When a photographic material (containing silver bromide) is subjected to prolonged exposure, a reaction will take place to such an extent that the photo-reacted silver causes a visible darkening. D. H. O. John & G. T. J. Field, *A Textbook of Photographic Chemistry*, London, Chapman & Hall Ltd., 1963. It is the silver from these darkened photographic film images which can be isolated and then quantitated by the spectrophotometric procedure.

An additional application of this invention is in quantitating the silver in bands in silver stained electrophoresis gels. By using the same method as used with X-ray films, a linear correlation is found between the amount of material in a given gel band and the amount of absorbance resulting from dithizone-silver complex formations. Since there is a need for an inexpensive and practical quantitation procedure, this method presents a convenient, inexpensive alternative to using a densitometer for quantitating images.

It is therefore a principal object of the invention to provide for a more economical method of quantitating the silver in silver stained bodies without the need for the highly specialized and expensive densitometer. Densitometers are relatively rare and expensive, often ranging from $15,000 to $30,000, whereas spectrophotometers are often comparatively inexpensive. Because the present invention utilizes a spectrophotometer, an instrument common to most laboratories, the process is convenient, rapid and inexpensive. Moreover, unlike a densitometer which is very limited in use because of its specialized purpose, a spectrophotometer has a multitude of uses beyond the applications of the present invention.

It is a further object of the invention to provide improved methods of determining relative amounts of silver in X-ray film images generated, for example, by autoradiography or chemiluminescence. Until now, the most common method of quantitating images in X-ray film was by using a densitometer. But, a densitometer is highly specialized and consequently limited in use in that it may be designed to accept only certain sizes and shapes of X-ray film. These limiting features make it prohibitively expensive for the casual user. The present invention overcomes these problems because direct quantitation of the X-ray image is achieved regardless of the size and shape of the X-ray film. Since the present invention requires the use of a spectrophotometer, a common fixture in biological and clinical laboratories, it provides a convenient, inexpensive alternative to using a densitometer. Thus. images on X-ray films can be quantitated in terms of the amount of silver that is present in the images.

It is yet a further object of the invention to provide improved methods of determining relative amounts of material in silver stained electrophoresis gels. Experiments with silver stained gels demonstrate that the amount of quantitated silver in a band in the gel relates to the amount of material represented by the band. Of course, this invention teaches a general method which contemplates many diverse applications. It may not only be applied in the fields such as biology and chemistry but can extend into many other fields, such as metallurgy and jewelry making, where it may be necessary to quantitate silver.

SUMMARY OF THE INVENTION

The method of quantitating images according to the invention generally includes the sequential steps of:
a) isolating the area of the image to be quantitated;
b) removing any silver which is present in the isolated area;
c) adding a complexing agent which binds to the removed silver and causes an optical change;
d) measuring the spectrophotometric absorbance; and P1
e) comparing the absorbance reading to calibrated reference standards.

The most convenient way of isolating the area of the image to be quantitated is by excising it from the X-ray film, electrophoresis gel or other material containing an image comprised of silver.

Silver which is present on the isolated area can be removed by conventional means known in the art. For example, oxidizing agents can be used such as nitric acid, and others as will be apparent to those skilled in the art.

Conventional complexing agents also can be employed such as diphenylthiocarbazone (dithizone), and others as will be apparent to those skilled in the art.

The spectrophotometric absorbance is measured by any suitable spectrophotometer and the calibrated reference standards can be prepared by various means; for example, a manufacturer of kits embodying the present invention can prepare the reference standards using solutions of known silver concentration to prepare calibration curves. Other means of preparing standardized reference materials will be apparent to those skilled in the art.

DETAILED DESCRIPTION OF THE INVENTION

Figure 1:
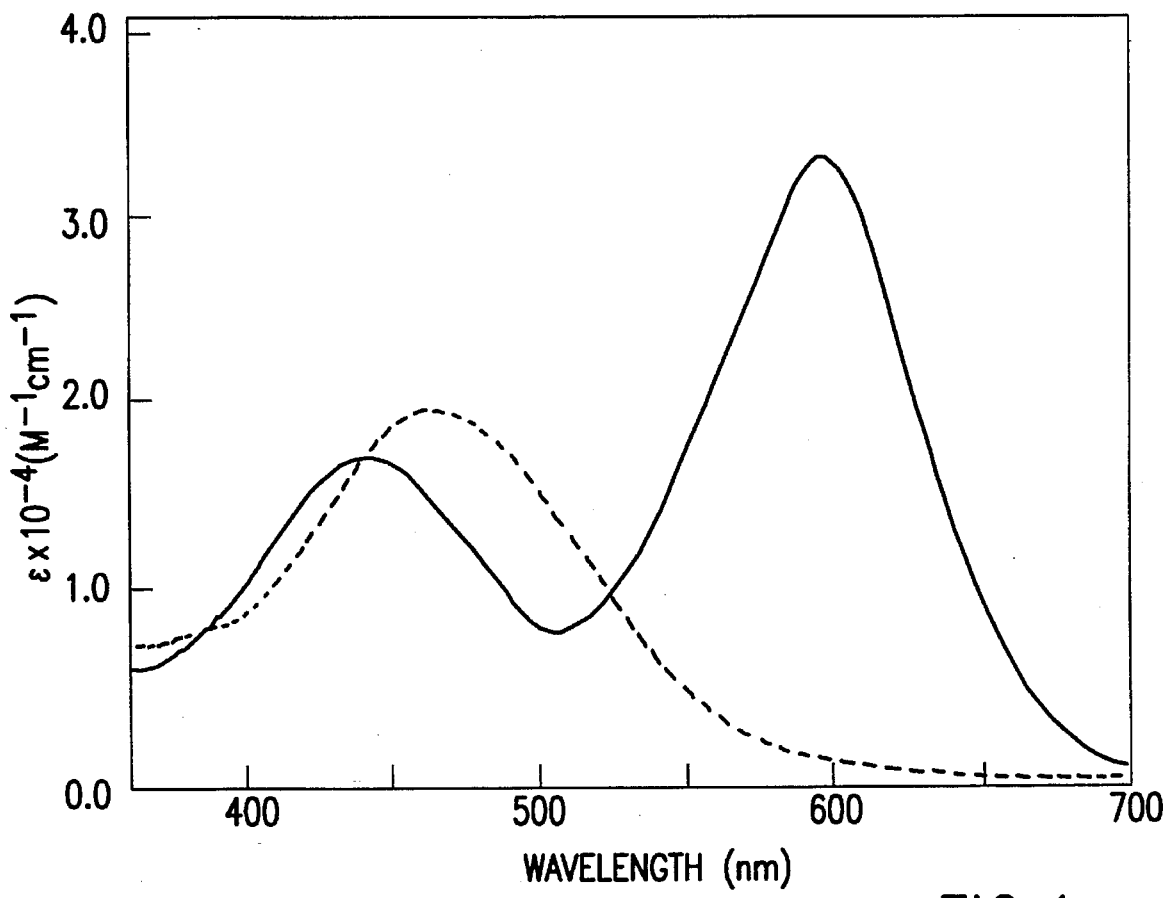
FIG. 1 is a visible spectra of dithizone (9.75 µM) in butanol before (solid line) and after (dashed line) extraction with a slight molar excess of silver acetate. In the extraction, a 400 µL solution of 97.5 µM dithizone in butanol was used to extract an 800 µL solution of 71.9 µM silver acetate in 1.0M sodium acetate, pH 4.0. A 100 µL aliquot of the resultant organic layer was diluted 10-fold in butanol to give a 9.75 µM dithizone solution for spectrophotometry.

In a preferred embodiment of the invention, a spot or band is cut from an X-ray film and immersed in 2.0 mL of 35% (v/v) $HNO_3$. (If the spot is very large, appropriate adjustments in volume can be made.) The metallic silver ($Ag^o$) oxidizes to ionic silver ($Ag^+$) which takes at most 20 minutes in the $HNO_3$. The pH of this solution then is adjusted by the following sequential additions:

1) 750 µL 1.0M sodium acetate, pH 4.0,
2) 25 µL 5.0M NaOH, and
3) 25 µL 35% (v/v) $HNO_3$ (final volume=800 µL).

Dithizone (400 µL of 0.02% dithizone in carbon tetrachloride) is added and the mixture is vigorously shaken. A 100 µL aliquot of the organic layer is added to 900 µL of carbon tetrachloride (final volume=1.0 mL) and the absorbance of the 1.0 mL mixture is read spectrophotometrically at 620 nm. The absorbance is compared to calibrated reference mixtures to determine the amount of silver in the spot or band and the amount of material (chemical or tissue) that the spot or band represents.

The foregoing steps can be varied, keeping in mind that the essence of the invention has to do with the binding of silver, which has been removed from a material containing an image comprising silver (such as an X-ray film or an electrophoresis gel), by a complexing agent causing a color change. Various methods of removing silver from the X-ray film could be used, and one could use other complexing agents which change color upon silver complexation. Other organic solvents also could be used as the diluent to reduce the concentration and increase the volume of the silver-dithizone complex (eg: acetonitrile, n-butanol and carbon tetrachloride).

Spectrophotometric absorbance readings can be taken at any suitable wavelengths that will enable the operator to obtain accurate reproducible results. Wavelengths ranging from about 590 to about 630 nanometers (nm) are suitable and a range from about 600 to about 620 nm is preferred. The most preferred wavelength is 620 nm.

It should be pointed out that the method of the invention depends critically on the amount of silver in an image being directly proportional to the amount of material represented by that image. Thus, for example, inaccuracies can be expected to occur when using overexposed films or over-stained gels in which the amount of silver in a spot or band may not be proportional to the amount of biomolecule it represents. Also, although quantitative comparisons of different images within a given gel or film are presumably valid, caution must be exercised when directly comparing the amount of silver from excised images from separate gels or films especially if they have not been exposed, developed, or silver stained for identical lengths of time.

Methods generally contemplated by the invention for the quantitation of silver include the steps of:

a) excising silver containing areas;

b) removing/oxidizing silver present in the silver containing areas with suitable agents to convert the silver into a form able to join with a complexing agent;

c) adding a solution of said complexing agent which binds to silver and produces an optical change;

d) measuring said optical change by spectrophotometric absorbance: and e) comparing the absorbance reading to calibrated reference standards.

In one specific embodiment of the invention a method for quantitating silver in silver images is disclosed comprising the steps of:

a) excising silver images;

b) oxidizing silver present in the silver images with an oxidizing agent to convert the silver into a form able to join with a complexing agent:

c) adding a solution of said complexing agent which binds to silver and produces an optical change;

d) measuring said optical change by spectrophotometric absorbance; and e) comparing the absorbance reading to calibrated reference standards.

In yet another specific embodiment of the invention, a method for quantitating silver in silver deposits is disclosed comprising the steps of:

a) excising silver containing areas;

b) oxidizing silver present in the silver containing areas with an oxidizing agent to convert the silver into a complex able to join with a complexing agent;

c) adding a solution of said complexing agent which binds to silver and produces an optical change;

d) measuring said optical change by spectrophotometric absorbance: and e) comparing the absorbance reading to calibrated reference standards.

In yet another specific embodiment a method for quantitating the amount of material represented by silver stained deposits is disclosed comprising the steps of:

a) excising silver containing areas;

b) oxidizing silver present in the silver containing areas with an oxidizing agent to convert the silver into a complex able to join with a complexing agent;

c) adding a solution of said complexing agent which binds to silver and produces an optical change;

d) measuring said optical change;

e) quantitating the concentration of silver present using a silver standard curve; and f) relating the amount of material present to the amount of quantified silver.

In still a further specific embodiment, a kit for quantitating silver in silver deposits is disclosed comprising:

a) silver standard solutions;

b) an oxidizing agent;

c) a complexing agent dissolved in a solvent:

d) a neutralizing reagent or reagents; and e) a diluent.

And finally, a specific method wherein a color change is linearly proportional to the amount of silver added to a complexing agent is disclosed.

These and other objects, features and advantages of the invention will become more apparent from the following examples.

EXAMPLE 1

Detection of Silver as Silver Acetate

It has been reported (Holmquist, 1988) that organic solutions of dithizone (diphenylthiocarbazone) change color when used to extract commonly-occurring adventitious metals from aqueous solutions. The color change results from electronic changes in dithizone upon binding to the metals. It has also been reported that dithizone can bind to silver ions. Based on these reports, we suspected that dithizone may change color upon binding silver ions and, if so, this color change might be useful in quantitating silver ions in solution.

As an initial test of the use of dithizone in silver quantitation, a standard solution of 46 ppm silver (pH adjusted to about 6) as silver acetate was made. A saturated solution of dithizone in carbon tetrachloride was also made. To 1.0 mL of various dilutions (0, 9.2, 27.6, 36.8, 46 ppm) of silver was added 0.2 mL of the dithizone solution. Upon mixing the organic phase containing silver, dithizone changed color to an extent dependent on the presence and concentration of silver in the aqueous phase. The dark green solution became increasingly darker red with increasing amounts of silver. A portion of the resultant organic layer (0.1 mL) was mixed with 0.9 mL of methanol and the red color was observed in a Hitachi U-3200 spectrophotometer (Danbury, Conn.). This initial experiment showed that it was conceivable that silver could be spectrophotometrically quantitated using dithizone.

EXAMPLE 2

Detection of Silver in an Autoradiogram

In many potential practical applications, silver is present not as ionic silver ($Ag^+$) but as metallic silver ($Ag^O$). Because dithizone binds ionic silver but not metallic silver, the metallic silver must be solubilized and oxidized to ionic silver to be detected. As a trial experiment, an autoradiogram was obtained. The autoradiogram was an X-ray film that had previously been exposed to $^{32}P$- labeled DNA fragments. The areas of the film exposed to radioactivity created latent images which were visualized by a standard method of X-ray film development. Pieces of the exposed and developed X-ray film were cut out using scissors. Some of the excised pieces did not have any visual dark spots and were used as unexposed controls. Other pieces had dark gray silver-containing bands generated by exposure to radiolabeled DNA. The pieces of film were immersed in 35% (v/v) nitric acid. The films quickly (in about 1 minute) became transparent as the metallic silver present became oxidized to water-soluble ionic silver. The films were removed from the solutions using tweezers and the acidic ionic silver solutions were neutralized with NaOH (dithizone binds to metals best in the neutral pH range). A saturated solution of dithizone in carbon tetrachloride was then added to each tube, the tubes were mixed, and the color of the organic phase containing dithizone was noted. It was found that the pieces of film containing silver (dark gray bands) caused the dithizone solution to turn red, whereas the control pieces had little effect on the color of the dithizone solution. Moreover, pieces containing silver-containing bands were of different sizes and it was found that the larger the piece (the more silver present), the darker red the dithizone solution became. This experiment demonstrated that metallic silver could be oxidized and solubilized into ionic silver that dithizone could bind to and the resulting complex would change color in relation to the amount of silver present.

EXAMPLE 3

Effect of Organic Solvent Used in Detection

The method was improved by obviating the use of the halogenated solvent, carbon tetrachloride. Other organic solvents were investigated for their ability to replace carbon tetrachloride. The main criteria for this were; 1) the solvent should be relatively non-toxic, 2) dithizone should be soluble in the solvent, and 3) when dissolved in the solvent, dithizone should bind tightly to silver and undergo an acceptable change in visible absorbance. In addition, it is preferable but not essential that the solvent be immiscible with water.

The organic solvents that were tested to replace carbon tetrachloride were; n-butyl alcohol, acetonitrile, methanol, and acetone. Acetone and methanol were not usable due to their miscibility with water and non-linear correlations between spectral changes and silver complexation in aqueous samples. In addition to carbon tetrachloride, acetonitrile and n-butanol produced good results. Butanol was chosen over acetonitrile for routine use for practical reasons. FIG. 1 shows the effect of silver acetate on the visible absorbance spectrum of dithizone in n-butanol. In one spectrum (solid line), 100 mL of a 97.5 mM solution of dithizone in n-butanol was diluted 10-fold in butanol and the spectrum was recorded. The dashed line spectrum shows the effect of ionic silver. A 400 mL solution of 97.5 mM dithizone in butanol was used to extract 800 mL of an aqueous solution (1.0M sodium acetate, pH 4.0) of 71.9 mM silver acetate. Following extraction, 100 mL of the dithizone-containing organic phase was diluted 10-fold in butanol and the spectrum was recorded. In the absence of silver, the color is blue-green and in the presence of a near stoichiometric (ionic silver:dithizone) amount of ionic silver, the color is yellow. (It should be noted that the colors of the organic solutions of dithizone vary from solvent to solvent). The change in the molar extinction coefficient (De) for the color change of dithizone in butanol at 600 nm was found to be $3.28 \times 10^4 M^{-1} cm^{-1}$. The complex formed rapidly upon vortexing and apparently has a very high affinity (as indicated by the complete spectral conversion in FIG. 1 upon addition of a little over one equivalent of silver). This dramatic color change suggested that silver could be readily quantitated using dithizone as a quantitative indicator. It is important to point out that if much greater than stoichiometric amounts of silver were added, the absorbance at 600 nm increased due to broadening and shifting of the peak that represents absorbance of the silver-dithizone complex (seen as $1_{max}$ of about 460 nm in FIG. 1), and the color becomes pink. This second color change, possibly indicating formation of higher order complexes, could be avoided by adjusting the concentration of silver used in quantitation to be less than the dithizone concentration.

EXAMPLE 4

Quantitation of Silver as Silver Acetate

The examples described above indicated that dithizone can be used for detection of metallic silver and ionic silver. For many applications, it is essential that the silver detection method is quantitative. Experiments were conducted to find conditions under which the observed dithizone color change is spectrophotometrically proportional to the amount of silver present in a solution or a solid. Initially, conditions were developed to spectrophotometrically quantitate ionic silver purchased as pure silver acetate (Sigma Chemical Co., St. Louis, Mo.).

Figure 2:
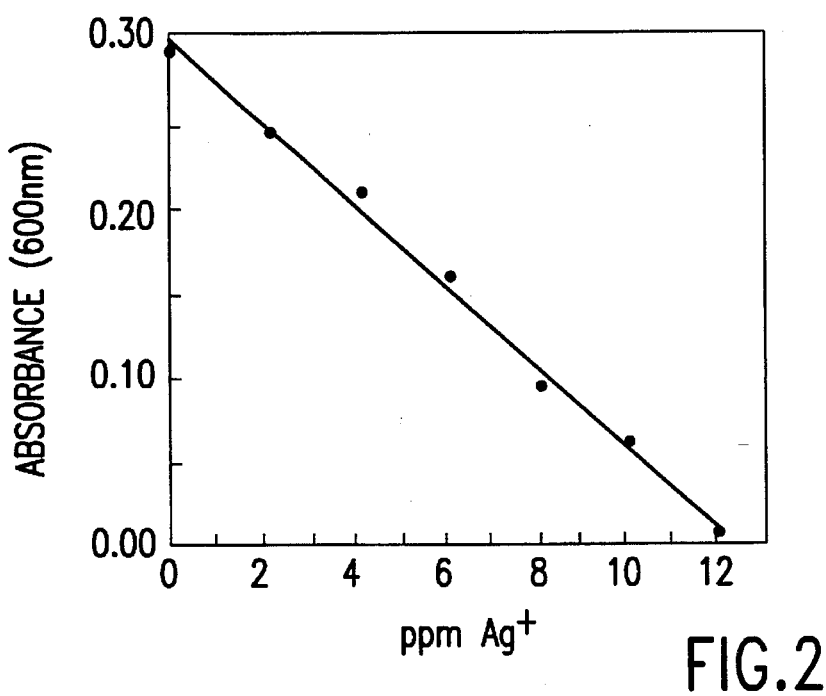
FIG. 2 is a standard curve demonstrating the effect of silver acetate concentration on the absorbance of dithizone at 600 nm. Various concentrations of silver acetate were extracted with 97.5 µM dithizone in butanol as described in the legend to FIG. 1. The resultant organic layers were diluted 10-fold in butanol and the absorbance was read at 600 nm.

FIG. 2 shows the spectrophotometric quantitation of ionic silver, as silver acetate. Under these conditions, the absorbance of the solution was found to be linearly dependent (R =0.997) on silver concentration over the range of 0 to 10 mg. The slope and absolute values of the absorbance readings were time dependent, owing to relative instability of the dithizone solution. It was best to use butanolic solutions of dithizone within 3 hours of preparation, to make absorbance measurements of the ionic silver-dithizone complexes within 20 minutes of formation, and to compare results with appropriate standard curves or controls made at the same time. In this and the examples below, all visible absorbance readings were carried out on a Hitachi U-3200 spectrophotometer (Danbury, Conn.).

EXAMPLE 5

Detection and Quantitation of Silver in Silver Stained Electrophoresis Gels

One of the potential applications of a silver quantitation method is the quantitation of material represented by spots in silver stained electrophoresis gels. Electrophoresis is a method of separating charged molecules such as biological macromolecules. It is common in the life sciences to electrophoretically separate proteins, DNA, and other biomolecules. In order to visualize these naturally invisible molecules on electrophoresis gels, various stains have been developed. One such commonly-used stain of proteins and DNA is the silver stain. By silver staining molecules, they become visible, even though they may be present at very low concentrations. Although silver staining is a detection method it is, by itself, not quantitative. In general, the darker the spots are stained, the more material (protein or DNA) is present. However, it can be difficult or impossible to quantitate the darknesses of silver stained spots by visual inspection.

In this experiment, an antibody (protein) electrophoresis gel was generated and silver stained by standard means. The antibody used in electrophoresis was a mouse monoclonal IgG antibody generated by conventional means for another study. Sodium dodecyl sulfate-polyacrylamide electrophoresis (SDS-PAGE) of the antibody preparation was performed using pre-cast, 1 mm thick, 4–20% acrylamide gradient EP minigels from Schleicher and Schuell (Keene, N.H.). Samples for electrophoresis were mixed with an equal volume of 2x-concentrated PAGE buffer containing b-mercaptoethanol and heated for 5 minutes at 95° C. Electrophoresis was carried out for 45 minutes at 200V. Gels were stained using the Silver Stain Plus kit (BioRad, Hercules, Calif.). The concentrations of antibody used in electrophoresis were determined by ELISA.

Silver stained bands from the electrophoresis gel was excised using a scalpel and the pieces of gel were suspended in 200 mL of 35% $HNO_3$ (v/v) to reduce the silver present from metallic silver to ionic silver. Solubilization was rapid and could be visibly monitored by the disappearance of the gray color from the gel. Aliquots of these solutions (200 mL) were mixed with a solution containing the same volume of 5.0M NaOH, and the necessary amount of 1.0M sodium acetate, pH 4.0, was added to adjust the volume to 800 mL. To each 800 mL of ionic silver solution was added 800 mL of freshly-made 97.5 mM dithizone in n-butanol (solutions of dithizone in butanol were used within 3 hours of preparation) and the samples were vigorously vortexed to facilitate complex formation. After separation from the aqueous phase, a 100 mL-aliquot of the organic layer was diluted 10-fold in n-butanol and the absorbance at 600 nm was read within 20 minutes. Silver concentration calibration curves were constructed using dilutions of silver acetate in a solution of 1.0M sodium acetate, pH 4.0.

Figure 3:
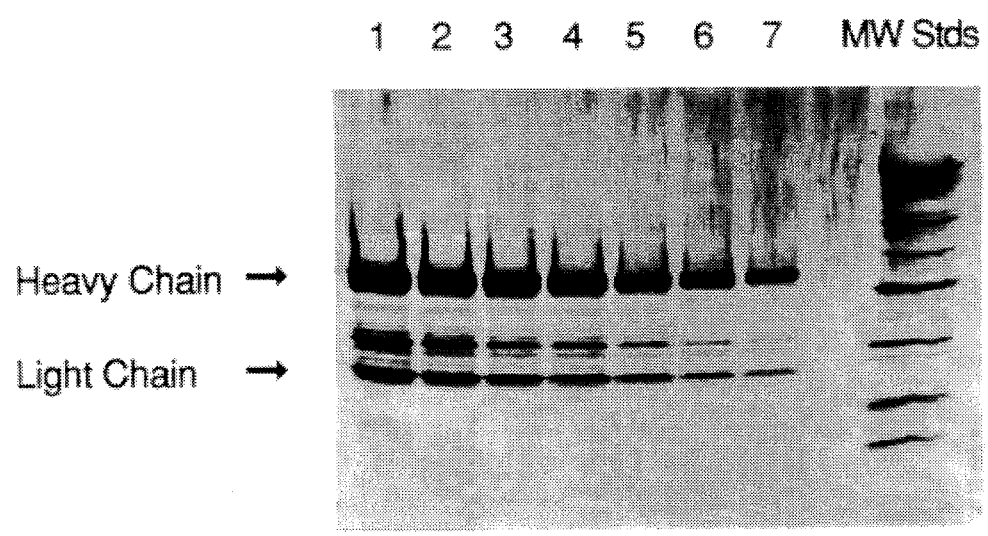
FIG. 3 is a silver stained electrophoresis gel of a preparation of immunoglobulin, where the amounts of protein were, from lane 1 to lane 7; 0.1, 0.2, 0.4, 0.8, 1.2, 1.6, 2.0 µg; and, molecular weight standards used were (from top to bottom in the right lane); phosphorylase b (97.4 kDa), bovine serum albumin (66.2 kDa), ovalbumin (45.0 kDa), carbonic anhydrase (31.0 kDa), soybean trypsin inhibitor (21.5 kDa), and hen egg lysozyme (14.3 kDa).
Figure 4:
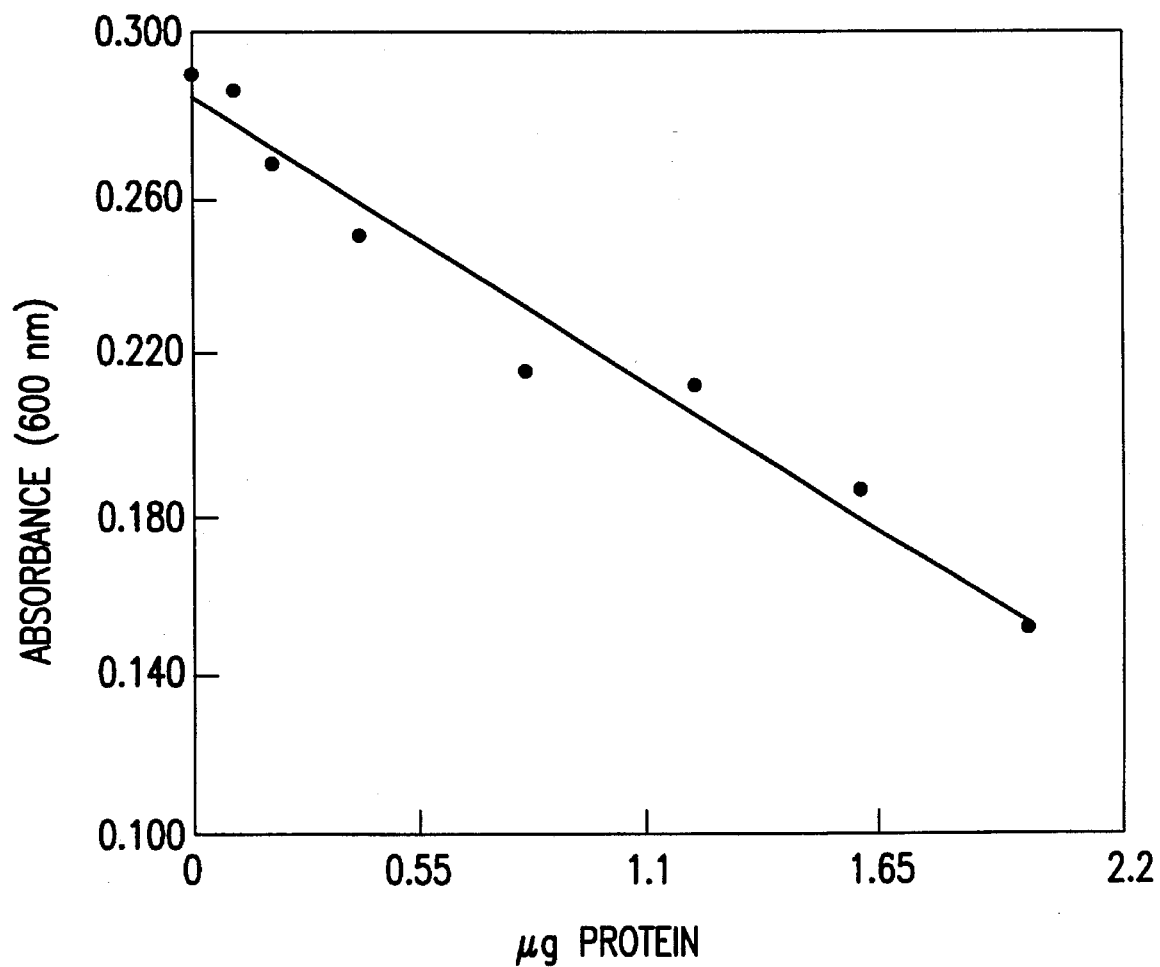
FIG. 4 is a comparison of the amount of protein applied to the gel as determined by ELISA with the amount of silver extracted from the light chain bands, whereby silver is quantitated using 200 µL of the acid extracts of the gel bands.

Silver in bands in the silver stained electrophoresis gel shown in FIG. 3 was quantitated (FIG. 4). A linear correlation (R=0.989) was found between the amount of protein in the gel bands and the visible absorbance of the resulting dithizone-silver complex (FIG. 4).

EXAMPLE 6

Detection and Quantitation of Silver in a Western Blot

Another application of silver quantitation is in X-ray films which are used in various professions and disciplines. X-ray film images contain metallic silver and the relative darknesses of the images are generally proportional to the amount of material represented by the image. Such films are commonly used in the life science research environment in autoradiography (detection of radioactively-labeled biomolecules) and in chemiluminescence (detection of molecules that emit light).

For purposes of method development, we used developed X-ray films that had been exposed to chemiluminescent Western blots. In the Western blot, a peroxidase-labeled goat anti-mouse antibody (Kirkegaard & Perry, Gaithersburg, Md.) was allowed to specifically bind to regions of a nitrocellulose membrane which contained various amounts of the mouse antibody to be quantitated. Using an Enhanced Chemiluminescence kit (ECL™) (Amersham, Arlington Heights, Ill.), the peroxidase catalyzed a chemiluminescent reaction that emitted light which was recorded on X-ray film. Because the light-emitting peroxidase was conjugated to the goat antibody which in turn was specifically bound to the mouse antibody, the generation of light marked the presence of the mouse antibody. ECL was performed according to manufacturers directions with appropriate dilutions of primary (mouse) and secondary (goat) antibodies to give an acceptable range of spot darknesses during detection. Before the experiment was begun, concentrations of the mouse antibody were determined by ultraviolet spectrophotometry. (A 1.0 mg/mL solution of IgG antibody was assumed to have an absorbance of 1.30 at 280 nm.)

Figure 5:
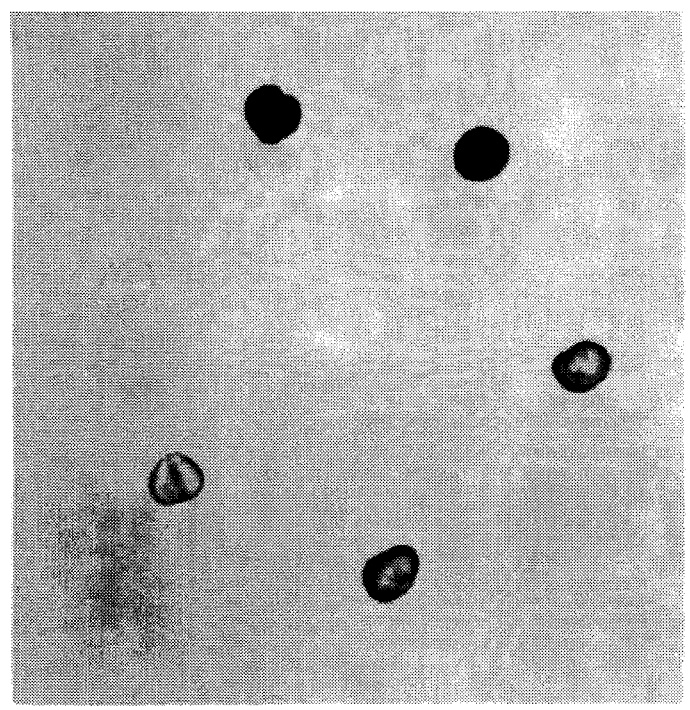
FIG. 5 is a X-ray film used in chemiluminescent detection of an antibody, where each spot represents a different concentration of antibody; from lightest to darkest spots the amount of antibody was 0.6, 1.2, 2.4, 3.7, 4.9 and 6.1 ng.
Figure 6:
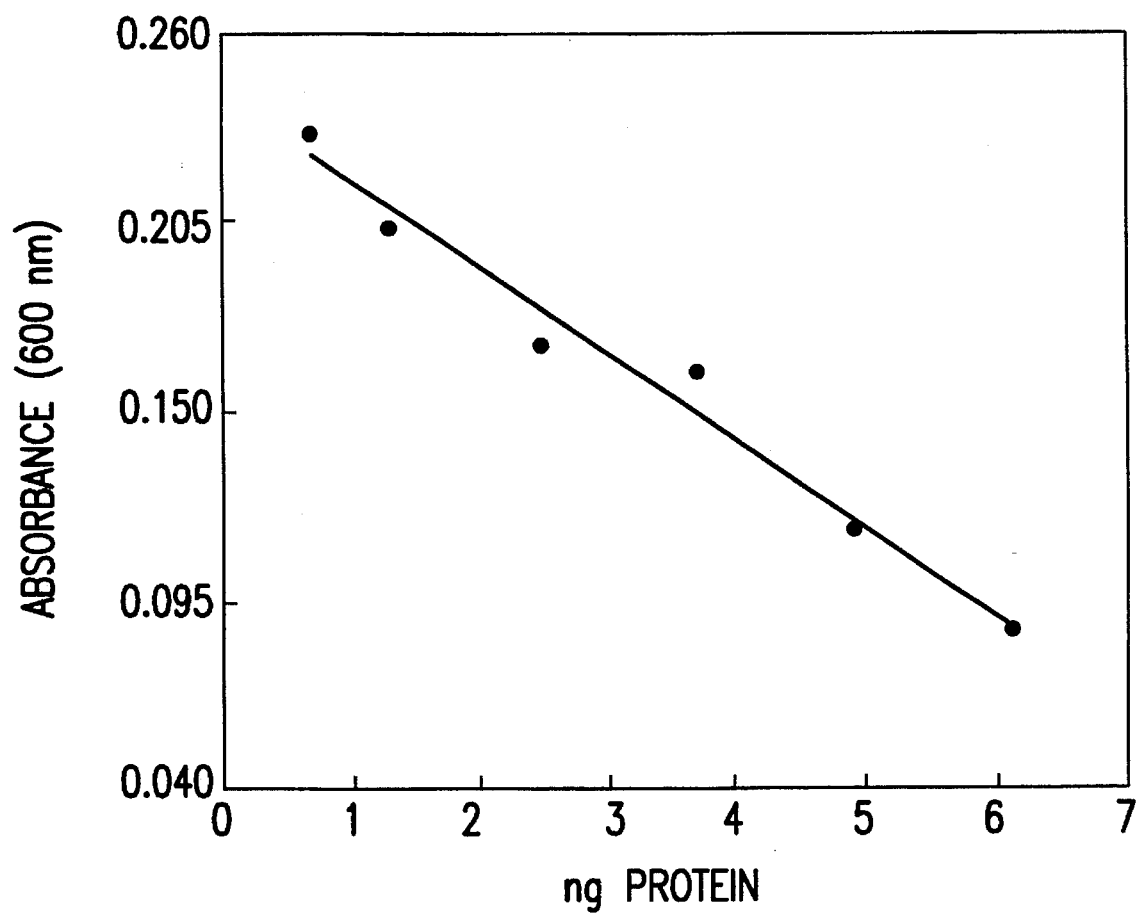
FIG. 6 is a comparison of the amount of primary antibody applied to a Western blot, as determined by absorbance at 280 nm, with the dithizone absorbance changes at 600 nm caused by complex formation with silver extracted from the X-ray film spots.

The developed film of one such experiment is shown in FIG. 5. Silver from the spots in FIG. 5 that had been exposed to ECL reactions were excised and suspended in 200 mL of 35% $HNO_3$ (v/v) to reduce the silver present from metallic silver to ionic silver. Solubilization was rapid and could be visibly monitored by the disappearance of the gray color from the film. Aliquots (2 mL) were mixed with a solution containing the same volume of 5.0 M NaOH, and the necessary amount of 1.0M sodium acetate, pH 4.0, was added to adjust the volume to 800 mL. To each 800 mL ionic silver solution was added 800 mL of freshly-made 97.5 mM dithizone in n-butanol and the samples were vigorously vortexed to facilitate complex formation. After separation from the aqueous phase, a 100 mL-aliquot of the organic layer was diluted 10-fold in n-butanol and the absorbance at 600 nm was read within 20 minutes. Silver concentration calibration curves were constructed using dilutions of silver acetate in a solution of 1.0M sodium acetate, pH 4.0. An aliquot of this silver solution was then added to a solution of dithizone in butanol, vortexed, and the organic layer was diluted ten-fold in butanol for spectrophotometric measurement. FIG. 6 shows that the resulting absorbance readings were linearly proportional to the amount of protein that was applied in the Western blot (R=0.986).

The size of the aliquot of the silver extract added to the dithizone solution must be considered because if more than one equivalent of silver (ionic silver:dithizone) was added, the relationship between silver concentration and absorbance change was no longer linear. In the results described above, a 200 mL aliquot of the silver extract was used in the gel band quantitation (FIG. 4) while a 2 mL aliquot was used in X-ray film spot quantitation (FIG. 6).

Having set forth the general nature and some specific examples of the invention, the scope of the invention is now more specifically set forth in the appended claims.

What is claimed is:

1. A method of quantitating images comprised of silver comprising the sequential steps of:

a) isolating an area of the image to be quantitated;

b) removing any silver which is present in the isolated area by converting the silver to a form suitable for binding a complexing agent and obtaining an extraction solution containing the removed silver;

c) adding a solution containing a complexing agent to the extraction solution to obtain a sample solution;

d) measuring an absorbance change between the extraction solution and the sample solution by spectrophotometry; and e) comparing the absorbance measurement to a calibrated reference standard.

2. The method of claim 1 wherein the area of the image to be quantitated is isolated by excising it from an X-ray film, electrophoresis gel or other material containing the image.

3. The method of claim 1 wherein the silver is removed with an oxidizing agent.

4. The method of claim 3 wherein the oxidizing agent is nitric acid.

5. The method of claim 1 wherein the complexing agent is an organic compound.

6. The method of claim 4 wherein the complexing agent is diphenylthiocarbazone.

7. The method of claim 1 wherein the absorbance is measured at from about 590 to about 630 nanometers.

8. A method of quantitating images comprised of silver in X-ray film or an electrophoresis gel comprising the sequential steps of:

a) excising the image from the film or gel:

b) removing any silver which is present in the excised image by converting the silver to a form suitable for binding a complexing agent and obtaining an extraction solution containing the excised silver;

c) adding a solution containing a complexing agent to the extraction solution to obtain a sample solution;

d) measuring an absorbance change between the extraction solution and the sample solution by spectrophotometry; and e) comparing the absorbance measurement to a calibrated reference standard.

9. The method of claim 8 wherein the image is a spot or band.

10. The method of claim 8 wherein the absorbance is measured at from about 590 to about 630 nanometers.

11. The method of claim 10 wherein the image is a spot or band.

12. The method of claim 11 wherein the silver is removed with an oxidizing agent.

13. The method of claim 12 wherein the oxidizing agent is nitric acid.

14. The method of claim 12 wherein the complexing agent is diphenylthiocarbazone.

15. A method of quantitating silver in silver containing spots, bands, or bodies from X-ray film or electrophoresis gel comprising the sequential steps of:
   a) excising silver containing areas;
   b) oxidizing silver present in the silver containing areas with an oxidizing agent to convert the silver into a form able to join with a complexing agent and obtaining an extraction solution containing the oxidized silver;
   c) adding a solution of said complexing agent which binds to silver and produces an optical change by spectrophotometric absorbance to the extraction solution to obtain a sample solution;
   d) measuring said optical change between the extraction solution and the sample solution; and
   e) comparing the optical change to a calibrated reference standard.

16. A method for quantitating the amount of material represented by silver stained deposits comprising the sequential steps of:
   a) excising silver containing areas;
   b) oxidizing silver present in the silver containing areas with an oxidizing agent to convert the silver into a form able to join with a complexing agent;
   c) adding a solution of said complexing agent which binds to silver and produces an optical change;
   d) measuring said optical change;
   e) quantitating an amount of silver present using a silver standard curve; and
   f) relating the amount of quantified silver to an amount of material present.

17. A method for quantifying the amount of a biomolecule present in a sample comprising:
   a) conducting an assay technique that includes staining an area of an assay device with silver from X-ray film or electrophoresis gel;
   b) removing the area stained with silver from the assay device;
   c) converting the silver into ionic silver and obtaining an extraction solution containing the ionic silver;
   d) adding a solution containing a complexing agent to the extraction solution to obtain a sample solution, said complexing agent being capable of changing color when bound to silver; and
   e) analyzing the amount of color change between the extraction solution and the sample solution.

18. A method for analyzing a silver-containing material comprising
   a) solubilizing a silver-containing material from X-ray film or electrophoresis gel into an ionic silver-containing component;
   b) extracting the ionic silver containing component in an organic solution;
   c) adding a solution containing a silver binding reagent to the organic solution to obtain a sample solution, said silver binding reagent having an absorbance pattern which is different than the absorbance pattern when the silver binding reagent is bound to silver;
   d) measuring the amount of absorbance difference between the organic solution and the sample solution.

19. The method of claim 18 wherein the ionic silver is $Ag^{30}$.

20. The method of claim 18 wherein the silver binding reagent is diphenylthiocarbazone.

21. The method of claim 18 wherein measuring the amount of absorbance difference includes spectrophotometrically quantitating the amount of silver.

22. A method for analyzing a silver-containing material comprising
   a) oxidizing a silver-containing material from X-ray film or electrophoresis gel and forming an oxidized solution containing ionic silver;
   b) adding the oxidized solution to an organic acid solution and extracting the ionic silver;
   c) adding a solution containing diphenylthiocarbazone to the organic acid solution to form a sample solution;
   d) allowing the ionic silver to bind to the diphenylthiocarbazone; and
   e) measuring the amount of absorbance difference between bound and unbound diphenylthiocarbazone.

* * * * *